United States Patent [19]

Veronesi et al.

[11] Patent Number: 5,580,576

[45] Date of Patent: Dec. 3, 1996

[54] PHARMACEUTICALLY/STORAGE-STABLE NICORANDIL FORMULATIONS

[75] Inventors: Paolo A. Veronesi; Anna M. Veronesi, both of Milan, Italy

[73] Assignee: Therapicon S.R.L., Milan, Italy

[21] Appl. No.: 73,054

[22] Filed: Jun. 8, 1993

[30] Foreign Application Priority Data

Jun. 8, 1992 [IT] Italy ................... MI92A1413

[51] Int. Cl.⁶ ............... A61K 9/48; A61K 9/66; A61K 9/64; A61K 31/455
[52] U.S. Cl. ............ 424/451; 424/455; 424/456; 424/472; 514/355
[58] Field of Search .................. 424/456, 472, 424/449, 451, 455; 514/355

[56] References Cited

U.S. PATENT DOCUMENTS 4,832,954  5/1989  Sato et al. .
5,057,317  10/1991  Iida .
5,112,604  5/1992  Beaurline et al. ............ 424/490
5,188,840  2/1993  Iida et al. .

*Primary Examiner*—Shean C. Wu
*Attorney, Agent, or Firm*—Burns, Doane, Swecker & Mathis, L.L.P.

[57] ABSTRACT

Pharmaceutically/storage-stable, water-resistant formulations of nicorandil comprise unit dosage coronary vasodilating amounts thereof in association, e.g., in suspension or in dispersion, with a pharmaceutically acceptable, characteristically low density dimethyl polysiloxane chemically compatible therewith, e.g., dimethicone or simethicone, are well suited for encapsulation within hard or soft gelatin capsules for oral/sublingual administration.

21 Claims, No Drawings

PHARMACEUTICALLY/STORAGE-STABLE NICORANDIL FORMULATIONS

BACKGROUND OF THE INVENTION

1. Field of the Invention

The present invention relates to pharmaceutically and storage-stable compositions of nicorandil comprising suspensions or dispersions of the active nicorandil agent in linear dimethyl polysiloxanes of low and medium density (dimethicone or simethicone), and, more especially, to hard and soft gelatin capsules charged with such formulations and to the pharmaceutical use of same as coronary vasodilations.

2. Description of the Prior Art

Nicorandil, the nitrate ester of N-(2-hydroxyethyl)nicotinamide, is a known coronary vasodilator, exerting a combined action suppressing coronary vasoconstriction and an inhibitory action on the coronary channels of calcium ions, as is evidenced by the considerable clinical data reported in the literature.

In the solid crystalline state, nicorandil is stable under conditions of extreme dryness, but when it is exposed, although for short periods of time and at room temperature, even at low humidity levels, a considerable instability ensues. The hydrolysis of nicorandil is catalyzed by three factors, each influencing the others, namely, the increased percentage of moisture in the product in powder state, the temperature and the storage period.

The progressive degradation of nicorandil entails the hydrolysis of the inorganic ester contained in the molecule, with the consequent liberation of nitric acid and of N-(2-hydroxyethyl)nicotinamide, a compound that is not pharmacologically active at the considered dosages, as evidenced by the substantial decrease in the content of the active ingredient and, therefore, of the pharmacological activity.

The degradation of nicorandil in the presence of water is so rapid that in aqueous solution at 5%, the product loses, at 60° C. and at pH 7 in only 12 hours, almost 20% of its titer. To the contrary, the powder in the dry state and under the same conditions of temperature, does not exhibit, during the same period, appreciable such quali-quantitative variations.

The same disadvantages and drawbacks reported for the raw material nicorandil are evidenced, albeit with more reduced intensity, during the preparation of conventional oral pharmaceutical forms (tablets), but the aforesaid phenomenon of degradation attains alarming levels during the subsequent storage periods.

The adoption of alternative techniques for the production of conventional tablets of nicorandil, containing variable amounts of saturated higher fatty acids, or of the inorganic salts thereof, or saturated higher alcohols (having a waxy or solid consistency at ambient temperatures), has provided slight improvements; however, the stability of nicorandil, when formulated in tablets, remains relatively precarious and unsatisfactory.

Moreover, the friction between the crystals of the product during the compression thereof, which occurs during the manufacture of the aforementioned preparations, has been described as a possible reason for the rupture of the crystals of nicorandil and of the consequent increased instability. This is indicated by Iida Yoshimitsu in European patent application No. 87/100,549.2 (publication 0 230 932 A2).

The use of completely moistureproof materials for the packaging of the tablets proves not only relatively expensive, but also insufficient to prevent the absorption of moisture and, therefore, to avoid the known degradation mechanisms of nicorandil therein contained, once the packaging of the pharmaceutical is opened.

In consideration of the clinico-therapeutic importance to maintain adequate dosages of nicorandil, when formulated in the adopted pharmaceutical forms, during periods of normal storage, specific studies have been conducted to develop improved formulations of nicorandil, which would be stable for an adequate period of time, thus not easily degradable, compatible with the excipients used for the formulation and, finally, preservable in conventional packaging materials, such as small glass or plastic bottles having screw caps, blister packaging or strips fabricated from thermosealed coupled foils of aluminum and copolymers.

During such research and the various attempts to provide stable preparations of nicorandil, the product has been suspended in variable amounts of triglycerides of aliphatic acids, saturated or unsaturated, having short and extended chains (from C-4 to C-12), linear or branched, monohydroxylated or not, or in variable amounts of polyglycolized glycerides of aliphatic saturated or unsaturated fatty acids, having medium-long chains (from C-8 to C-22), linear or branched, monohydroxylated or not, or in mixtures of variable amounts of the above glycerides and polyglycolized glycerides, the above vehicles being in a liquid or semi-solid state at ambient temperatures.

The above dispersions have been used to fill hard gelatin capsules (preferably having a sealing band) or soft gelatin capsules and the resulting pharmaceutical dosage forms showed an appreciable increase of stability. Moreover, this particular preparative technique avoids the compression of the active ingredient which, as above indicated, is a possible cause of the instability of the nicorandil when it is compressed. The concentrations of nicorandil in these compositions may vary in a percentage ranging from 1% to 50%. The indicated triglycerides may be individual compounds or mixtures thereof in variable proportions of conventional esters well known to this art, having the following general formula:

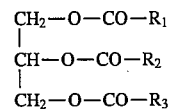

wherein $R_1$, $R_2$ and $R_3$ are the residues of aliphatic fatty acids, typically C-4 to C-12 in length, optionally unsaturated and typically comprising from 1 to 6 double bonds, or optical, position or other isomers thereof. The polyglycolized glycerides are mixtures of esters, in different proportions, of conventional compounds, well known to this art, such esters having the following H.L.B. (Hydrophilic-Lipophilic-Balance) values:

|  | H.L.B. values |
| --- | --- |
| Triglycerides | from 1 to 2 |
| Diglycerides | from 2 to 3 |
| Monoglycerides | from 3 to 4 |
| Diesters of polyethylene glycol | from 6 to 15 |
| Monoesters of polyethylene glycol | from 10 to 17 | wherein the proportion of the five ingredients are characterized by the composition of the reaction mixture. The numbers of amphophily are expressed as H.L.B. (Hydrophilic-Lipophilic-Balance) values (from 1 to 17). The principal aliphatic acids most commonly esterified with the medium chain triglycerides (from C-8 to C-12) and with the saturated polyglycolized glycerides, are, preferably, selected from among the saturated fatty acids, lauric acid, myristic acid, palmitic acid, stearic acid and arachidic acid, from among the unsaturated fatty acids, lauroleic acid, myristoleic acid, palmitoleic acid, oleic acid, linoleic acid and linolenic acid, from among the branched acids, isostearic acid, and from among the monohydroxylated, ricinoleic acid.

The stability studies in respect of the abovedescribed formulations of nicorandil in any event evidenced that the samples stored at temperatures of about 40° C. developed, after an interval of some weeks, a considerable decrease in the assay of the active ingredient nicorandil. This phenomenon has been actively studied and it has been determined that nicorandil interacts with the triglycerides of the fatty acids, saturated or unsaturated, having short-medium chain (from C-4 to C-12), linear or branched, monohydroxylated or not, and/or with the polyglycolized glycerides of aliphatic fatty acids, having medium-long chain (from C-8 to C-22), saturated or unsaturated, linear or branched, monohydroxylated or not, by virtue of a transesterification which effects the hydrolysis of nicorandil with formation of different esters of N-(2-hydroxyethyl)nicotinamide (primary aminoalcohol) with one or more fatty acids resulting from the triglyceride and/or from the polyglycolized glyceride (compounds definitely not active pharmacologically) and the simultaneous substitution of the fatty acid with nitric acid, also emanating from the nicorandil. This phenomenon is determined by high pressure liquid chromatography, whereby it is possible to determine, as soon as the transesterification of the nicorandil occurs, multiple peaks corresponding to the various resulting compounds, having different retention times which are much greater than nicorandil itself. Contrariwise, Iida Yoshimitsu, in European patent application No. 87/100,549.2 (publication 0 230 932 A2) describes formulations of nicorandil tablets, the excipients in which comprise considerable amounts of long-chain aliphatic saturated acids, or of the inorganic salts thereof, or higher aliphatic saturated alcohols, solid at ambient temperatures, optionally including a certain amount of a unique organic acid. The dissolution profile of these formulations containing only nicorandil with higher aliphatic saturated acids or higher saturated alcohols, also admixed with other conventional excipients, which only exert the function of a support, does not prove to be particularly satisfactory and, with a view towards enhancing the dissolution profile of the tablet, it is also described to include a deaggregating agent in the subject compositions or, preferably, an organic acid.

Despite the efforts to control the moisture content below the normal (3–5%), such tablets of nicorandil showed a certain instability, which is evidenced also in this case with a decrease in the assay of nicorandil during normal storage periods.

Furthermore, insufficient dissolution of the aforesaid tablets may be a disadvantage for this type of active ingredient, for which rapid absorption and a rapid pharmacological and vasodilating response are often required.

Thus, serious need continues to exist in this art for preparations of nicorandil exhibiting better stability and rapid bioavailability, not only via the oral route, but also by sublingual administration. Indeed, the ideal pharmaceutical formulation for nicorandil would serve as a protective barrier, to prevent the external humidity from contacting the active ingredient and wherein any excipients would additionally protect the nicorandil from the external humidity, but would also be inert and chemically compatible therewith, to avoid any interactions which may inactivate the product, as in the case of the transesterification indicated above with the triglycerides of the fatty acids and/or the polyglycolized glycerides of aliphatic acids.

SUMMARY OF THE INVENTION

Accordingly, a major object of the present invention is the provision of unique nicorandil formulations that are improvedly pharmaceutically/storage-stable.

Briefly, the present invention features the use of the dimethyl polysiloxanes (also designated simethicone or dimethicone) as surprisingly effective excipients for nicorandil compositions, the same being stable during storage, since they are chemically inert and therefore do not interact with the "nitrate ester" function of the molecule of nicorandil, are hydrorepellent and serve as a valuable protective barrier, isolating nicorandil against the exogenous humidity, both factors otherwise contributing to a rapid degradation of the compound.

Moreover, the dimethyl polysiloxanes are resistant to heat, to the action of atmospheric agents (oxygen, ozone, water and light), possess an appreciable absence of toxicity and a good tolerability, all characteristics which are well suited to avoid the degradation processes of nicorandil.

The present invention also features suspensions of nicorandil in dimethyl polysiloxanes encapsulated within soft or hard gelatin capsules, the shells of which providing an additional protection barrier for the nicorandil/dimethyl polysiloxane suspensions, especially against the external moisture.

DETAILED DESCRIPTION OF PREFERRED EMBODIMENTS OF THE INVENTION

More particularly according to the present invention, the concentrations of nicorandil in the suspensions of dimethyl polysiloxanes advantageously range from a minimum of 0.5% to a maximum of 50% by weight.

The pharmaceutically acceptable dimethyl polysiloxanes according to the invention, for example those defined in the *European Pharmacopoeia*, volume 11, page 138 as "dimethiconum" or "dimethicone" and in the *French Pharmacopoeia*, 9th edition, as "low and medium density silicone oils," are advantageously linear dimethyl polysiloxanes (polymers) having the following linear structural formula:

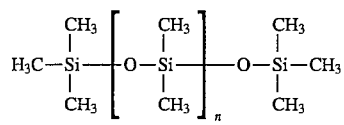

in which the degree of polymerization may range from n=20 to 400, while their nominal kinematic viscosity at 25° C. may range from 20 mm$^2$×S$^{-1}$ to 1,000 mm$^2$×S$^{-1}$ (from 20 cSt to 1,000 cSt) (±5%). Dimethicone is prepared via the prior art techniques of hydrolysis and polycondensation of dichloromethylsiloxane and of chlorotrimethylsilane.

Different types of polysiloxanes exist, which are differentiated by means of the nominal viscosity thereof, which is represented by an indication following the name of the substance. Moreover, dimethicone is a product commercially available under different grades of density. Additionally, dimethicone is colorless, odorless and, thus, also possesses ideal organoleptic characteristics. The more preferred suspensions of nicorandil in dimethyl polysiloxanes, providing a satisfactory and uniform distribution of the active ingredient, are formulated from a dimethicone having a viscosity of 50 (±5%), due to the fact that the dimethyl polysiloxanes with higher viscosity may cause production problems during the operations of repartition of the suspensions.

The suspensions of nicorandil in dimethicone may conventionally be encapsulated in soft or in hard gelatin capsules (with a sealing band being provided therefor). The soft or hard gelatin capsules which are filled with the above suspensions of nicorandil are conventional to this art, manufactured via known technique, containing gelatin, glycerol and, optionally, titanium dioxide, preserving and coloring agents. Moreover, the soft or hard gelatin capsules selected permit unit dosage amounts to be incorporated therein and administration of the exact amounts of nicorandil. Unit dosage amounts of 5 mg, 10 mg and 20 mg are representative.

To provide a better homogeneity of the suspension of nicorandil in dimethyl polysiloxane and the uniformity of the therapeutically effective amount, desirable to improve the operation of repartition of the suspension in the capsules, small amounts of Aerosil (a brand of colloidal silicon dioxide) or of lecithin are added to the formulation, which increases the suspendibility of the active ingredient in the dimethyl polysiloxanes. Moreover, the colloidal silica may entrap the humidity eventually present, or which may be introduced into the suspension inside the capsule during storage, thus preempting the water interacting with the nicorandil and effecting possible degradation processes of hydrolytic type. The percentage by weight of colloidal silica in the above compositions may advantageously range from 0.5% to 20%.

Further, sweetening agents may optionally be added to the above compositions, such as sugar, cyclamates, saccharins and aspartame and natural or synthetic flavoring agents or essences, provided they are chemically compatible with the other active ingredients of the composition, in order to ensure that the suspensions of nicorandil are more palatable and acceptable, in the event that the contents of the capsule are provided for sublingual administration, after chewing the capsule with the teeth, thus retaining the liquid in the oral cavity.

Exemplary suspensions of the invention exhibiting better suitability for repartition in gelatin capsules, are the following:

| Suspension | 5% | 10% | 20% |
|---|---|---|---|
| Nicorandil | 5.000 mg | 10.000 mg | 20.000 mg |
| Dimethicone | 91.833 mg | 87.833 mg | 78.917 mg |
| Colloidal silica | 3.167 mg | 2.167 mg | 1.083 mg |
| Weight of the suspension | 100.000 mg | 100.000 mg | 100.000 mg |

As regards the shell of the soft gelatin capsule, the following compositions are well suited for the manufacture thereof:

| Gelatin | 50.400 mg | 50.400 mg | 50.400 mg |
|---|---|---|---|
| Glycerol | 24.304 mg | 24.304 mg | 24.304 mg |
| Titanium dioxide E171 | 0.799 mg | 0.799 mg | 0.300 mg |
| Iron oxide, red E172 | 0.020 mg | 0.200 mg | 0.799 mg |
| Weight of shell | 75.523 mg | 75.703 mg | 75.803 mg |

The suspensions of the present invention thus comprise the essential active ingredients nicorandil and dimethicone and, as optional constituents, silica, sweetening agents, flavoring agents and/or essences. The subject compositions of nicorandil present the advantage of surprising stability even during relatively long storage periods. The soft or hard gelatin capsules which are filled with these suspensions of nicorandil are conventional, produced via conventional prior art technique, containing gelatin and, optionally, glycerol, titanium dioxide, preserving agents and colorants. The hard or soft gelatin capsules permit administering the precise amounts of the active ingredient nicorandil, whether in unit dosage amounts of 5 mg, 10 mg or 20 mg (±10%).

In order to further illustrate the present invention and the advantages thereof, the following specific examples are given, it being understood that same are intended only as illustrative and in nowise limitative.

EXAMPLE 1

Preparation of 1,800 Soft Gelatin Capsules, Size 2 Oval, Containing 5 mg of Nicorandil:

A filling suspension was prepared, having the following composition, corresponding to the individual content of a soft gelatin capsule containing 5 mg of nicorandil:

| Nicorandil | 5.000 mg |
|---|---|
| Dimethicone (viscosity cSt 50 ± 5%) | 91.833 mg |
| Colloidal silica (Aerosil) | 3.167 mg |
| Total weight of the contents | 100.000 mg |
| The external shell was prepared from: | |
| Gelatin | 50.400 mg |
| Glycerol | 24.304 mg |
| Titanium dioxide E171 | 0.799 mg |
| Iron oxide, red E172 | 0.020 mg |
| Total weight of the shell | 75.523 mg |

Nicorandil (9.0 g), after sieving on a 30 mesh sieve, and silica (5.7 g) were accurately suspended in dimethicone V Cst 50 (165.3 g) and the formulation was intimately admixed to complete homogeneity. The weight of the resulting mixture was about 180.0 grams. The suspension then obtained was charged, under constant stirring, into the supply tank of a dosing loop for liquid suspensions of a machine for the production of soft gelatin capsules. The soft gelatin capsules were filled with the suspension via conventional technique, in No. 2 capsules, oval in shape. The soft gelatin capsules obtained (1,705 of which / yield 94.7%) were collected in stainless steel trays and stabilized (dehydrated) according to conventional methods. The soft gelatin capsules were then preserved in amber glass bottles, having screw caps, at a temperature of 40° for 180 days and analyzed at 90 days and at the end of the storage period.

For purposes of comparison, reference tablets (about 1,000 tablets) were prepared according to conventional methods, having the following conventional formulation:

| Nicorandil | 5.000 mg |
|---|---|
| Mannitol | 71.700 mg |
| Starch | 20.000 mg |
| Methylcellulose | 0.300 mg |
| Magnesium stearate | 3.000 mg |
| Total weight of the tablet | 100.000 mg |

Mannitol (71.7 g), starch (20.0 g), methylcellulose (0.3 g) and nicorandil (5.0 g) were accurately mixed in a polyethylene bag. Then the magnesium stearate (3.0 g) was added and after a brief (about 3 minutes) period of mixing, the mixture was compressed directly using suitable punch in order to obtain tablets having a mean unit weight of about 100.0 mg.

The reference tablets produced (953 of which / yield 95.3%) were packaged in separate amber glass bottles, having screw caps, preserved at 40° C. for 180 days and analyzed at 90 days and at the end of the storage period.

The assay of nicorandil in the samples of soft gelatin capsules of the present invention and in the reference tablets was determined by suitable high pressure liquid chromatographic technique, in order to determine the content of active ingredient during and at the end of the period of storage and, thus, to compare the stability of the two formulations. The amount of active ingredient was expressed as % of the initial assay (considered as 100%), determined after the production, before the storage period.

The results obtained are reported in the following Table I and evidence that the soft gelatin capsules of the invention exhibited appreciable stability during the indicated storage period, much higher than the normal reference tablets, preserved under the same conditions.

TABLE I

Stability study of soft gelatin capsules and of reference tablets of Example 1, dosed at 5 mg of nicorandil, expressed as assay % of the initial figure (mean figure obtained from the determination of 10 units of each pharmaceutical form):

| Compositions | Initial (% of theoretical) | Storage Intervals | |
|---|---|---|---|
| | | 90 days | 180 days |
| Soft gelatin capsules | 99.76 | 99.15 | 98.91 |
| Reference tablets | 99.08 | 85.92 | 67.24 |

EXAMPLE 9

Preparation of 2,500 Soft Gelatin Capsules, Size 2 Oval, Containing 10 mg of Nicorandil:

A filling suspension having the following composition was prepared, corresponding to the individual content of a soft gelatin capsule containing 10 mg of nicorandil:

| | |
|---|---|
| Nicorandil | 10.000 mg |
| Dimethicone (viscosity cSt 50 ± 5%) | 87.833 mg |
| Colloidal silica (Aerosil) | 2.167 mg |
| Total weight of contents | 100.000 mg |
| The external shell had the composition: | |
| Gelatin | 50.400 mg |
| Glycerol | 24.304 mg |
| Titanium dioxide E171 | 0.799 mg |
| Iron oxide, red E172 | 0.200 mg |
| Total weight of the shell | 75.703 mg |

Nicorandil (25.0 g), after sieving on a 30 mesh sieve, and silica (5.4 g) were accurately suspended in dimethicone V cSt 50 (219.6 g) and the formulation was intimately admixed to complete homogeneity. The weight of the resulting mixture was about 250.0 grams. The suspension thus obtained was charged, under constant stirring, into the supply tank of a dosing loop for liquid suspensions of a machine for the production of soft gelatin capsules. The soft gelatin capsules were filled with the suspension via conventional technique, in No. 2 capsules, oval in shape. The soft gelatin capsules produced (2,384 of which / yield 95.36%) were collected in stainless steel trays and stabilized (dehydrated) according to conventional methods. The soft gelatin capsules were then preserved in amber glass bottles, having screw caps, at a temperature of 40° C. for 180 days and analyzed at 90 days and at the end of the storage period.

For purposes of comparison, reference tablets (about 1,000 tablets) were prepared according to conventional methods, containing the following conventional formulation:

| | |
|---|---|
| Nicorandil | 10.000 mg |
| Mannitol | 68.000 mg |
| Starch | 10.000 mg |
| Calcium carboxymethylcellulose | 6.000 mg |
| Hydroxypropylcellulose | 3.000 mg |
| Calcium stearate | 3.000 mg |
| Total weight of the tablet | 100.000 mg |

Mannitol (68.0 g), starch (10.0 g), calcium carboxymethylcellulose (6.0 g), hydroxypropylcellulose (3.0 g) and nicorandil (10.0 g) were accurately mixed in a polyethylene bag. Then the calcium stearate (3.0 g) was added and after a brief (about 3 minutes) period of mixing and the mixture was compressed directly using a suitable punch in order to obtain tablets having a mean unit weight of about 100.0 mg.

The obtained reference tablets (947 of which / yield 94.7%) were packaged in separate amber glass bottles, having screw caps, preserved at 40° C. for 180 days and analyzed at 90 days and at the end of the storage period.

The assay of nicorandil in the samples of soft gelatin capsules of this invention and in the reference tablets was determined by suitable high pressure liquid chromatographic technique, in order to determine the content of active ingredient during and at the end of the storage period and, thus, to compare the stability of the two formulations.

The amount of active ingredient was expressed as % of the initial assay (considered as 100%), determined after production, prior to the storage period.

The results obtained are reported in the following Table II and evidence that the soft gelatin capsules of the invention exhibited an appreciable stability during the indicated storage period, much higher than the normal reference tablets, preserved under the same conditions.

TABLE II

Stability study of soft gelatin capsules and of reference tablets of Example 2, dosed at 10 mg of nicorandil, expressed as assay % of the initial figure (mean figure obtained from the determination of 10 units of each pharmaceutical form):

| Compositions | Initial (% of theoretical) | Storage Intervals | |
|---|---|---|---|
| | | 90 days | 180 days |
| Soft gelatin capsules | 99.53 | 98.82 | 98.64 |

TABLE II-continued

| Reference tablets | 99.72 | 85.16 | 69.10 |

EXAMPLE 3

Preparation of 3,000 Soft Gelatin Capsules, Size 2 Oval, Containing 20 mg of Nicorandil:

A filling suspension having the following composition was prepared, corresponding to the individual content of a soft gelatin capsule dosed at 20 mg of nicorandil:

| | |
|---|---|
| Nicorandil | 20.000 mg |
| Dimethicone (viscosity cSt 100 ± 5%) | 80.000 mg |
| Total weight of the contents | 100.000 mg |

The external shell had the following composition:

| | |
|---|---|
| Gelatin | 50.400 mg |
| Glycerol | 24.304 mg |
| Titanium dioxide E171 | 0.300 mg |
| Iron oxide, red E172 | 0.799 mg |
| Total weight of the shell | 75.803 mg |

Nicorandil (60.0 g), after sieving on a 30 mesh sieve, was accurately suspended in dimethicone V cSt 100 (240.0 g) and the mixture was stirred to complete homogeneity. The weight of the resulting mixture was about 300.0 grams.

The suspension then obtained was charged, under constant stirring, into the supply tank of the dosing loop for liquid suspensions of a machine for the production of soft gelatin capsules. The soft gelatin capsules were filled with the suspension via conventional technique, in No. 2 capsules oval in shape. The soft gelatin capsules obtained (2,765 of which / yield 92.16%) were collected in stainless steel trays and stabilized (dehydrated) according to conventional methods. The soft gelatin capsules were then preserved in amber glass bottles, having screw caps, at a temperature of 40° C. for 180 days and analyzed at 90 days and at the end of the storage period.

For purposes of comparison, reference tablets (about 1,000 tablets) were prepared according to conventional methods, having the following conventional formulation:

| | |
|---|---|
| Nicorandil | 20.000 mg |
| Lactose | 65.000 MG |
| Starch | 9.000 mg |
| Croscarmellose sodium | 5.000 mg |
| Magnesium stearate | 1.000 mg |
| Total weight of the tablet | 100.000 mg |

Lactose (65.0 g), and croscarmellose sodium (5.0 g) were accurately mixed in a mortar and then kneaded with starch glue (9.0 g in about 15.0 ml of water). The wet mixture was granulated by means of a 30 mesh screen and then dried at about 50° C. for about 5 hours. The dried granulate was sieved on a 30 mesh sieve, in order to obtain a uniform granulometry.

Nicorandil (20.0 g) and magnesium stearate (1.0 g) were added and mixed in a polyethylene bag and the mixture was compressed directly using a suitable punch (pressure about 1,000 kg) in order to obtain tablets having a mean unit weight of about 100.0 mg.

The reference tablets (952 of which / yield 95.2%) were packaged in separate amber glass bottles, having screw caps, maintained at 40° C. for 180 days and analyzed at 90 days and at the end of the storage period.

The titer (amount of active ingredient found by the assay) of nicorandil in the samples of soft gelatin capsules of this invention and in the reference tablets was determined by suitable high pressure liquid chromatographic technique, in order to determine the content of active ingredient during and at the end of the storage period and, thus, to compare the stability of the two formulations. The quantity of active ingredient was expressed as % of the initial assay (considered as 100%), determined after the production, prior to the storage period.

The results obtained are reported in the following Table III and evidence that the soft gelatin capsules of the invention exhibited an appreciable stability during the storage period under consideration, much higher than the normal reference tablets, preserved under the same conditions.

TABLE III

Stability study of soft gelatin capsules and of reference tablets of Example 3, dosed at 20 mg of nicorandil, expressed as assay % of the initial figure (mean figure obtained from the determination of 10 units of each pharmaceutical form):

| Compositions | Initial (% of theoretical) | Storage Intervals | |
|---|---|---|---|
| | | 90 days | 180 days |
| Soft gelatin capsules | 99.63 | 99.21 | 98.94 |
| Reference tablets | 99.77 | 83.14 | 65.88 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pharmaceutically/storage-stable composition of matter, comprising an effective coronary vasodilating amount of nicorandil formulated in a pharmaceutically acceptable dimethyl polysiloxane compatible therewith which composition is substantially free of water.

2. The pharmaceutically/storage-stable nicorandil composition as defined by claim 1, said dimethyl polysiloxane comprising a low or medium density silicone oil having the formula:

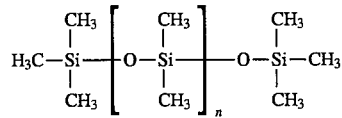

in which n ranges from 20 to 400.

3. The pharmaceutically/storage-stable nicorandil composition as defined by claim 1, comprising from 0.5% to 50% by weight of said nicorandil.

4. The pharmaceutically/storage-stable nicorandil composition as defined by claim 3, comprising about 5 mg of said nicorandil.

5. The pharmaceutically/storage-stable nicorandil composition as defined by claim 3, comprising about 10 mg of said nicorandil.

6. The pharmaceutically/storage-stable nicorandil composition as defined by claim 3, comprising about 20 mg of said nicorandil.

7. The pharmaceutically/storage-stable nicorandil composition as defined by claim 1, further comprising from 0.5% to 20% by weight of colloidal silica or lecithin.

8. The pharmaceutically/storage-stable nicorandil composition as defined by claim 1, further comprising an organoleptically effective amount of a sweetener, flavorant, essence, or admixture thereof.

9. The pharmaceutically/storage-stable nicorandil composition as defined by claim 1, encapsulated within a hard or soft gelatin capsule.

10. The pharmaceutically/storage-stable nicorandil composition as defined by claim 1, comprising a suspension or dispersion of said nicorandil in said dimethyl polysiloxane.

11. The pharmaceutically/storage-stable nicorandil composition as defined by claim 1, adopted for oral administration.

12. The pharmaceutically/storage-stable nicorandil composition as defined by claim 1, adopted for sublingual administration.

13. A method of eliciting a coronary vasodilating response in a patient in need of such treatment, comprising administering thereto the pharmaceutically/storage-stable nicorandil composition as defined by claim 1.

14. The composition of claim 1, wherein said composition consists essentially of Nicorandil admixed with a pharmaceutically acceptable dimethyl polysiloxane compatible therewith.

15. A pharmaceutically acceptable storage-stable composition of matter in the form of a dispersion or suspension consisting essentially of Nicorandil and a liquid dimethyl polysiloxane which is substantially free of water, which dimethyl polysiloxane possesses a viscosity ranging from 20 mm$^2$/S to 100 mm$^2$/S and wherein the concentration of Nicorandil therein ranges from about 0.5% to 50%.

16. The composition of claim 15, wherein the dimethyl polysiloxane comprises a low or medium density silicone oil having the formula:

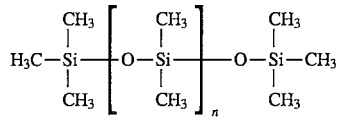

wherein n ranges from 20 to 400.

17. The composition of claim 15, which further comprises colloidal silica or lecithin.

18. The composition of claim 17, wherein the amount of colloidal silica ranges from 0.5% to 20%.

19. The composition of claim 18, wherein the amount of colloidal silica ranges from 1% to 20%.

20. The composition of claim 17, wherein the amount of lecithin ranges from 0.5% to 20%.

21. The composition of claim 20, wherein the amount of lecithin ranges from 1% to 10% by weight.

* * * * *

UNITED STATES PATENT AND TRADEMARK OFFICE
CERTIFICATE OF CORRECTION

PATENT NO. : 5,580,576

DATED : December 3, 1996

INVENTOR(S) : Paolo A. VERONESI et al.

It is certified that error appears in the above-identified patent and that said Letters Patent is hereby corrected as shown below:

In column 5, line 61 move "red E172" up one line so that is directly under "Iron oxide," and leave a line after the phrase "red E172" to separate it from the phrase "Weight of shell".

In column 5, line 67, change "ingredients" to --ingredient--.

In column 6, line 31, change "contents" to --content--.

Col. 7, line 45 delete "EXAMPLE 9" to --EXAMPLE 2--.

In column 7, line 56, change "contents" to --content--.

In column 9, line 19, change "contents" to --content--.

In column 9, line 52, change "65.000 MG" to --65.000 mg--.

Signed and Sealed this

Fourteenth Day of April, 1998

Attest:

BRUCE LEHMAN

*Attesting Officer*  *Commissioner of Patents and Trademarks*